US008026098B2

(12) United States Patent
Cranenburgh et al.

(10) Patent No.: US 8,026,098 B2
(45) Date of Patent: Sep. 27, 2011

(54) PROCESS FOR THE REMOVAL OF SELECTABLE MARKER GENE SEQUENCES

(75) Inventors: Rocky Marc Cranenburgh, Keele (GB); Alexandra Elizabeth Bloor, Keele (GB)

(73) Assignee: Cobra Biologics Limited, Keele (GB)

( * ) Notice: Subject to any disclaimer, the term of this patent is extended or adjusted under 35 U.S.C. 154(b) by 612 days.

(21) Appl. No.: 11/631,319

(22) PCT Filed: Jul. 1, 2005

(86) PCT No.: PCT/GB2005/002590
§ 371 (c)(1),
(2), (4) Date: Apr. 12, 2007

(87) PCT Pub. No.: WO2006/003412
PCT Pub. Date: Jan. 12, 2006

(65) Prior Publication Data
US 2007/0259430 A1    Nov. 8, 2007

(30) Foreign Application Priority Data

Jul. 1, 2004  (GB) .................................. 0414832.6

(51) Int. Cl.
C12N 15/00 (2006.01)
C12N 15/87 (2006.01)
C12N 15/74 (2006.01)
(52) U.S. Cl. ......... 435/462; 435/455; 435/463; 435/471
(58) Field of Classification Search ........................ None
See application file for complete search history.

(56) References Cited

U.S. PATENT DOCUMENTS
2004/0219629 A1* 11/2004 Cheng et al. .................... 435/67

FOREIGN PATENT DOCUMENTS
WO      01/18222       3/2001
WO      2004/056973    7/2004

OTHER PUBLICATIONS

Ferrer et al (Journal of Bacteriology, Feb. 1996, p. 951-960.*
Blakely et al. JBC vol. 75, No. 14, p. 9930-9936, 2000.*
International Search Report for PCT/GB2005/002590 mailed Dec. 8, 2005.
Blakely et al., *Escherichia coli XerC Recombinase Is Required for Chromosomal Segregation at Cell Division*, The New Biologist, vol. 3, No. 8, Aug. 1991, pp. 789-798.
Barre et al., *FtsK functions in the processing of a Holliday junction intermediate during bacterial chromosome segregation*, Genes & Development, Dec. 1, 2000, vol. 14, No. 23, pp. 2976-2988, XP002355143.
Recchia et al., *FtsK-dependent and -independent pathways of Xer site-specific recombination*, The Embo Journal, Oct. 15, 1999, vol. 18, No. 20, pp. 5724-5734, XP002355144.

Villion Manuela et al., *The XerC recombinase of Proteus mirabilis: characterization and interaction with other tyrosine recombinases*, FEMS Microbiology Letters, Sep. 12, 2003, vol. 226, No. 1, pp. 65-71, XP002355145.
Recchia et al., *Conservation of xer site-specific recombination genes in bacteria*, Molecular Microbiology, Dec. 1999, vol. 34, No. 5, pp. 1146-1148, XP002355146.
Schweizer, *Applications of the Saccharomyces cerevisiae Flp-FRT system in bacterial genetics*, Journal of Molecular Microbiology and Biotechnology, 2003, vol. 5, No. 2, pp. 67-77, XP009057378.
Bregu et al, "Accessory factors determine the order of strand exchange in Xer recombination at *psi*", The EMBO Journal, vol. 21, No. 14, pp. 3888-3897, 2002.
Cornet et al, Plasmid pSC101 Harbors a Recombination Site, *psi*, Which Is Able to Resolve Plasmid Multimers and to Substitute for the Analogous Chromosomal *Escherichia coli* Site *dif*, Journal of Bacteriology, Jun. 1994, p. 3188-3195, vol. 176, No. 11.
Cranenburgh et al, "*Escherichia coli* strains that allow antibiotic-free plasmid selection and maintenance by repressor titration", Nucleic Acids Research, 2001, vol. 29, No. 5 e26.
Cox et al, "The importance of repairing stalled replication forks", Nature, vol. 404, Mar. 2, 2000, pp. 37-41.
Dale et al, "Gene transfer with subsequent removal of the selection gene from the host genome", Proc. Natl. Acad. Sci., vol. 88, pp. 10558-10562, Dec. 1991.
Datsenko et al, "One-step inactivation of chromosomal genes in *Escherichia coli* K-12 using PCR products", PNAS, Jun. 6, 2000, vol. 97, No. 12, pp. 6640-6645.
Hanak et al, "Antibiotic-free plasmid selection and maintenance in bacteria", Recombinant Protein Production wit Prokaryotic and Eukaryotic Cells, 2001, 111-124.
Jasin et al, "Deletion of an Essential Gene in *Escherichia coli* by Site-Specific Recombination with Linear DNA Fragments", Journal of Bacteriology, Aug. 1984, vol. 159, No. 2, p. 783-786.
Leenhouts et al, "A general system for generating unlabelled gene replacements in bacterial chromosomes", Mol Gen Genet (1996) 253:217-224.
Leslie et al, "Site-specific recombination in the replication terminus region of *Escherichia coli*: functional replacement of *dif*", The EMBO Journal, vol. 14, No. 7, pp. 1561-1570, 1995.
Link et al, "Methods for Generating Precise Deletions and Insertions in the Genome of Wild-Type *Escherichia coli*: Application to Open Reading Frame Characterization", Journal of Bacteriology, Oct. 1997, vol. 179, No. 20, pp. 6228-6237. McCulloch et al, Xer-mediated site-specific recombination at *cer* generates Holiday junctions in vivo, The EMBO Journal, vol. 13, No. 8, pp. 1844-1855, 1994.
Murphy et al, "Use of Bacteriophage • Recombination Functions to Promote Gene Replacement in *Escherichia coli*", Journal of Bacteriology, Apr. 1998, vol. 180, No. 8, pp. 2063-2071.
Sanchis et al, "A Recombinase-Mediated System for Elimination of Antibiotic Resistance Gene Markers from Genetically Engineered *Bacillus thuringiensis* Strains", Applied and Environmental Microbiology, Feb. 1997, vol. 63, No. 2, pp. 779-784.
Sciochetti et al, "Identification and Characterization of the *dif* Site from *Bacillus subtilis*", Journal of Bacteriology, Feb. 2001, vol. 183, No. 3, pp. 1058-1068.
Somerville et al, "A Novel *Escherichia coli* Lipid a Mutant That Produces an Antiinflammatory Lipopolysaccharide", J. Clin. Invest., vol. 97, No. 2, Jan. 1996, pp. 359-365.

(Continued)

*Primary Examiner* — Oluwatosin Ogunbiyi
(74) *Attorney, Agent, or Firm* — Nixon & Vanderhye P.C.

(57) ABSTRACT

The invention relates to a process for the removal of selectable marker gene sequences, in particular antibiotic gene sequences, from nucleic acid molecules. The invention further relates to the application of this process in the unlabelled integration and deletion of chromosomal genes and in controlling gene expression.

18 Claims, 5 Drawing Sheets

OTHER PUBLICATIONS

Sugita et al, "A transformation vector for the production of marker-free transgenic plants containing a single copy transgene at high frequency", The Plant Journal (2000) 22(5), 461-469.

Williams et al, "Repressor titration: a novel system for selection and stable maintenance of recombinant plasmids", Nucleic Acids Research, 1998, vol. 26, No. 9, 2120-2124.

Winans et al, "Site-Directed Insertion and Deletion Mutagenesis with Cloned Fragments in *Escherichia coli*, "Journal of Bacteriology, Mar. 1985, vol. 161, No. 3, pp. 1219-1221.

Bloor et al, "An Efficient Method of Selectable Marker Gene Excision by Xer Recombination for Gene Replacement in Bacterial Chromosomes", Applied and Environmental Microbiology, Apr. 2006, vol. 72, No. 4, p. 2520-2525.

Cascioferro et al., "Xer Site-Specific Recombination, an Efficient Tool to Introduce Unmarked Deletions into Mycobacteria" Applied and Environmental Microbiology, Aug. 2010, vol. 76, No. 15, p. 5312-5316.

Cranenburgh, "Antibiotic-Free Systems for Production: Bypassing the Expression of Exogenous Site-Specific Recombinases" GEN Bioprocessing Technote, Genetic Engineering News, Aug. 2006, p. 66.

Recipharm CobraBio, "Rapid and Universal Genetic Modification of Bacteria: Xer-cise™", (2011) RecipharmCobra Biologics, UK.

* cited by examiner

A)

B)

M. kb DNA ladder
1. Negative control (no DNA)
2. Wild type (DH1 gDNA)
3. Integrant gDNA (DH1::ΔmsbB-DifCAT)
4.-7. Resolvant clones (DH1ΔmsbB)

A)

B)

M. kb DNA ladder
1. Negative control (no DNA)
2. Wild type (DH1*lacdapD* gDNA)
3. Integrant gDNA (DH1*lacdapD*::rbpA-DifCAT)
4.-7. Resolvant clones (DH1*lacdapD*-rbpA)

PROCESS FOR THE REMOVAL OF SELECTABLE MARKER GENE SEQUENCES

This application is the US national phase of international application PCT/GB2005/002590 filed 1 Jul. 2005, which designated the U.S. and claims benefit of GB 0414832.6, filed 1 Jul. 2004, the entire contents of each of which are hereby incorporated by reference.

FIELD OF THE INVENTION

The invention relates to a process for the removal of selectable marker gene sequences, in particular antibiotic gene sequences, from nucleic acid molecules. The invention further relates to the application of this process in the unlabelled integration and deletion of chromosomal genes and in controlling gene expression.

All documents referred to herein are incorporated by reference.

BACKGROUND OF THE INVENTION

Antibiotic resistance genes or other selectable marker genes are routinely used to select for the chromosomal insertion of heterologous genes or the deletion of native genes to create new strains of bacteria. These selectable marker genes are also routinely used to select for the presence of plasmids in bacterial cells. However, the retention of selectable marker genes in bacterial host cells, whether they are integrated into the chromosome or present on plasmids, gives rise to a number of problems.

Firstly, the presence of selectable marker genes in the host chromosome reduces the variety of plasmids that can be propagated in a cell, as these also rely on selectable marker genes for their selection and maintenance. Furthermore, genetically modified bacteria containing chromosomal antibiotic resistance genes are undesirable for biotherapeutics production, in particular for DNA vaccine and gene therapy applications, as the chromosomal DNA will represent a low-level contaminant of the final product and carry the risk of antibiotic gene transfer to pathogenic bacteria in the patient or the environment. Antibiotic resistance genes on plasmids are also undesirable, as they constitute a metabolic burden in recombinant protein production and a biosafety concern when the plasmid is being manufactured for use in gene therapy and DNA vaccine applications.

It is thus highly desirable to be able to insert genes into or delete genes from bacterial cell chromosomes without leaving antibiotic resistance or other selectable marker genes behind and to be able to remove these selectable marker genes from plasmids when they are no longer required. To date, a couple of strategies have been developed for unlabelled (i.e. selectable marker gene-free) chromosomal gene insertions and deletion in bacterial cells and for deletion of marker genes from plasmids.

One strategy for unlabelled gene insertion and deletion relies on integrating a plasmid containing a selectable marker gene into the bacterial host cell chromosome via a single homologous recombination event, followed by the removal of the plasmid by a second recombination event (resolution) to hopefully produce the desired genotype (Leenhouts et al. 1996; Link et al., 1997). A major disadvantage with this approach is that if the insertion or deletion reduces the fitness of the cell in terms of its ability to survive, the resolution event will invariably regenerate the wild type rather than the mutant genotype. This approach is therefore highly inefficient.

An alternative strategy is to use a double recombination event to efficiently integrate an antibiotic resistance gene cassette flanked by regions of chromosomal homology into the bacterial chromosome. Recognition sites for a site-specific recombinase (SSR) immediately flank the antibiotic resistance gene. Following chromosomal integration, a recombinase expressed in trans excises the antibiotic resistance gene. Examples of site-specific recombinases/target sites used for antibiotic gene excision include Cre/loxP from the bacteriophage P1 (Dale and Ow, 1991), FLP/FRT (Datsenko and Wanner, 2000) and R/RS (Sugita et al., 2000) from yeast. Alternatively, flanking antibiotic resistance genes with internal resolution sites enables excision by a transposase expressed in trans (Sanchis et al., 1997). The disadvantage of this strategy is that it requires an exogenous recombinase or transposase to be expressed in the target cell. The cell must therefore be transformed twice.

Selectable marker genes are currently also removed from plasmids using site-specific recombinases as described for the chromosomal applications above, or, more commonly, by restriction endonuclease digestion. The recombinase approach requires an additional site-specific recombinase gene to be present in cis or on a helper plasmid in trans. The restriction digest approach requires several extra stages of plasmid DNA manipulation. Both these approaches involve a number of complex manipulations.

Given the increasing importance of generating nucleic acid molecules without selectable marker genes, in particular antibiotic resistance genes, there is a need to develop improved and simpler processes for unlabelled gene insertion and deletion and for removing selectable marker genes from plasmids.

SUMMARY OF THE INVENTION

According to a first aspect of the invention, there is provided a process for removing a selectable marker gene from a nucleic acid molecule in a cell comprising culturing a cell comprising a nucleic acid molecule comprising a selectable marker gene flanked by site-specific recombinase recognition sites under conditions such that an endogenous site-specific recombinase in the cell acts to excise the selectable marker gene by site-specific recombination between the site-specific recombinase recognition sites. Preferably, the site-specific recombinase recognition sites are dif-like sites.

Prokaryotic cells contain endogenous site-specific recombinases that resolve chromosomal dimers generated by RecA. These recombinases are XerC/XerD in gram-negative bacteria such as *Escherichia coli* (Leslie and Sherratt, 1995) and RipX/CodV in gram-positive bacteria such as *Bacillus subtilis* (Sciochetti et al. 2001). These endogenous site-specific recombinases act at dif sites present in the prokarytic chromosome. A single dif site is normally present in a prokarotic chromosome. When chromosomal dimers are generated, the site-specific recombinase acts to promote recombination between two dif sites to excise the intervening DNA and generate chromosome monomers.

Endogenous prokaryotic site-specific recombinases such as XerC/XerD and RipX/CodV also resolve plasmid dimers generated by RecA by acting at dimer resolution sites that occur naturally in plasmids. For example, the ColE1 plasmid contains a dimer resolution site called cer and the pSC 101 plasmid contains a dimer resolution site called psi. When plasmid dimers are formed, endogenous site-specific recombinases act to excise the DNA between two dimer resolution sites, resulting in plasmid monomers. However, unlike dif sites, the site specific recombinases only act on plasmidborne dimer resolution sites if accessory sequences of ~200 bp are also present on the plasmid (Hayes and Sherratt, 1997).

Eukaryotic cells also contain endogenous site-specific recombinases which act to excise DNA between two site-specific recombinase recognition sites. For example, the Flp recombinase of the yeast two-micron plasmid acts to monomerise concatomers by excising DNA between FRT sites.

Experimental investigations into the mechanism of action of site-specific recombinases at dif sites in prokaryotes have shown that these site-specific recombinases also act to excise DNA between tandem dif sites present on a plasmid or on a prokaryotic chromosome (Barre et al., 2000, Recchia et al., 1999). However, there has been no suggestion that endogenous site-specific recombinases could be used in genetic engineering to provide an improved process of unlabelled gene integration and deletion and to provide a simplified process for removing selectable marker genes from plasmids.

The process of the first aspect of the invention exploits the ability of endogenous site-specific recombinases in cells to act on site-specific recombinase recognition sites, preferably dif-like sites, to remove selectable marker genes from a nucleic acid molecule without introducing an exogenous recombinase in trans as required by current processes for removing selectable marker genes.

The cell in which the process of the first aspect of the invention is carried out may be any cell containing endogenous site-specific recombinases that act at site-specific recombinase recognition sites. The cell may be a prokaryotic cell or a eukaryotic cell. Preferably, the cell is a prokaryotic cell that contains endogenous site-specific recombinases that act at dif-like sites. Preferably, the endogenous site-specific recombinases in the prokaryotic cell that act at dif-like sites are present in the chromosome of the prokaryotic cell.

Where the cell is a prokaryotic cell, it is preferably a bacterial cell which may be a gram negative bacterial cell or a gram positive bacterial cell. Gram negative bacterial cells useful according to the invention include, but are not limited to cells from *E. coli, Shigella, Vibrio* and *Salmonella*, e.g. *Salmonella typhimurium*. Preferably, the gram negative bacterial is an *E. coli* cell. *E. coli* cells contain the XerC/XerD site-specific recombinases that act at dif-like sites. Gram positive bacterial cells useful according to the invention include, but are not limited to *Bacillus, Streptomyces, Listeria, Mycobacterium, Lactobacillus* and *Lactococcus*. Preferably the gram positive bacterial cell is a *Bacillus subtilis* cell. *B. subtilis* cells contain the RipX/CodV site-specific recombinases that act at dif-like sites. Where the cell is a prokaryotic cell, it may be a RecA+ cell or a RecA- cell. Preferably, the cell is a RecA+ cell. Where the cell is a eukaryotic cell, it is preferably a yeast cell.

As used herein, the term "site-specific recombinase recognition site" includes any site which, when present in tandem in a nucleic acid molecule, is capable of being acted on by endogenous site-specific recombinases in the cell in which the process of the first aspect of the invention to excise the portion of the nucleic acid molecule between the tandem sites and produce a nucleic acid molecule containing a single site-specific recombinase site. The site-specific recombinase recognition sites flanking the selectable marker gene may be the same or different.

Preferably, the site-specific recombinase recognition sites are dif-like sites. The term dif-like sites" refers to site-specific recombinase recognition sites which are dimer resolution sites that are capable of being acted on by endogenous site-specific recombinases in prokaryotic cells in which the process of the first aspect of the invention is carried out. The dif-like sites flanking the selectable marker gene may be the same or different.

A preferred site-specific recombinase recognition site is the FRT site from yeast. Preferred dif-like sites include dif sites found in bacterial chromosomes, such as the dif site from the *E. coli* chromosome (Cornet et al., 1996) and the dif site from the *B. subtilis* chromosome (Sciochetti et al. 2001). Additional preferred dif-like sites include dif-like sites found in bacterial plasmids, such as the cer site from the *E. coli* plasmid ColEI, or the psi site from the *Salmonella* plasmid pSC101 (Cornet et al., 1996). The sequences of these dif-like sites are provided in Table 1 below. However, it will be apparent to the skilled person that dif-like sites other than those listed in Table 1 from other cell chromosomes and plasmids may also be used in the process of the invention.

The invention also encompasses the use of hybrid dif-like sites formed by combining naturally-occurring dif-like sites from plasmids and chromosomes. An example of such a hybrid site is the dif-psi hybrid site also known as the pif site (Cornet et al., 1996), the sequence of which is given in Table 1 below. Further hybrid sites for use in the process of the invention may be developed by generating hybrid sequences and determining the ability of these hybrid sequences to act as dif-like sites using simple recombination tests such as those described by Barre et al, 2000.

Where the dif-like sites used in the process of the invention are derived from a plasmid, the nucleic acid molecule must further comprise accessory sequences that are required for the site-specific recombinases to act. These accessory sequences are 180 bp binding sites for the proteins PepA and ArgR which are described in Pham et al, 2002 and Bregu et al, 2002.

TABLE 1

| Exemplary dif-like sites for use in the invention | |
|---|---|
| Site name (and origin) | Sequence (5'-3') |
| Ecdif (*E. coli* chromosome) | GGTGCGCATAATGTATATTATGTTAAAT (SEQ ID NO: 1) |
| cer (*E. coli* plasmid ColEI) | GGTGCGTACAATTAAGGGATTATGGTAAAT (SEQ ID NO: 2) |
| psi (*Salmonella* plasmid pSC101) | GTGCGCGCAAGATCCATTATGTTAAAC (SEQ ID NO: 3) |
| pif (dif-psi hybrid) | GGTGCGCGCAAGATCCATTATGTTAAAT (SEQ ID NO: 4) |
| Bsdif (*B. subtilis* chromosome) | ACTTCCTAGAATATATATTATGTAAACT (SEQ ID NO: 5) |

It will be apparent to the skilled person that the nature of the site-specific recombinase recognition sites, preferably dif-like sites, included in the nucleic acid molecule in the process of the first aspect of the invention will depend on the site-specific recombinases that are endogenous to the cell in which the process is taking place. The process provides an advantage over prior art processes in that it does not require the introduction of an exogenous recombinase in trans. The site-specific recombinase recognition sites must therefore be capable of being acted on by endogenous site-specific recombinases in the cell in which the process is taking place. However, this does not mean that the site-specific recombinase recognition sites must also be endogenous to the cell in which the process is taking place. For example, there is evidence that site-specific recombinases from one species are able to act at dif-like sites from other species (Neilson et al, 1999). In addition, site-specific recombinases have been shown to resolve dif-like sites that are different (Cornet et al, 1994), e.g. an E. coli dif site and a psi-dif hybrid. The site-specific recombinase recognition sites, preferably dif-like sites, flanking the selectable marker gene may therefore be the same or different. The skilled person will be capable of selecting or developing site-specific recombinase recognition sites, preferably dif-like sites, to use to flank the selectable marker gene so that the process of the invention can take place.

The selectable marker gene may be any gene which can be used to detect the presence of the nucleic acid molecule. In general, antibiotic resistance genes are used in the art to identify cells containing a particular nucleic acid molecule, be it a plasmid or a linear DNA cassette integrated into the chromosome. Preferably, the selectable marker gene is therefore an antibiotic resistance gene which allows identification of cells containing the nucleic acid molecule by culture in a medium containing the antibiotic. Antibiotic resistance genes are known in the art and any of these genes may be used. Examples of antibiotic resistance genes which may be used include, but are not limited to, genes which convey resistance to kanamycin, ampicillin, chloramphenicol, tetracycline, neomycin, blasticidin, hygromycin, puromycin and zeocin.

Preferably, the process of the first aspect of the invention comprises culturing the cell in the presence of selective pressure on the selectable marker gene and subsequently removing the selective pressure on the selectable marker gene. Culturing the cell in the presence of a selective pressure on the selectable marker gene allows selection of cells containing the nucleic acid molecule comprising the selectable marker gene. Removal of the selective pressure on the selectable marker gene allows cells in which site-specific recombination to excise the selectable marker gene has taken place to survive. Where the selectable marker gene is an antibiotic resistance gene, the process of the invention thus preferably comprises culturing said cell in the presence of the antibiotic to select for cells containing the nucleic acid molecule and subsequently culturing said cell in the absence of the antibiotic.

According to a further embodiment of the process of the first aspect of the invention, the nucleic acid molecule may further comprise a second gene that allows positive selection of cells from which the selectable marker gene has been excised. Preferably, the second gene that allows positive selection is incorporated adjacent to the selectable marker gene, with both genes flanked by site-specific recombinase recognition sites, preferably dif-like sites, such that both genes are excised if site-specific recombination takes place. Where the nucleic acid molecule comprises a second gene that allows positive selection of cells from which the selectable marker gene has been excised, the process preferably further comprises culturing the cell under conditions such that cell death occurs if the second gene (and hence the selectable marker gene) have not been excised.

Suitable genes that allow positive selection include genes that are toxic to the cell under certain conditions. For example, the sacB gene expresses the enzyme levansucrase that coverts sucrose into a compound that is toxic to E. coli (Link et al., 1997). A cell comprising a nucleic acid molecule comprising an antibiotic resistance gene and a sacB gene flanked by site-specific recombinase recognition sites may be cultured in the presence of the antibiotic to select for cells containing the nucleic acid molecule. The cells may subsequently be cultured in the absence of the antibiotic, allowing survival of cells in which the antibiotic resistance gene has been excised as well as cells in which no recombination has taken place. If the cells are then plated onto nutrient agar containing sucrose, any cell that has not lost both the antibiotic resistance gene and the sacB gene as a result of recombination between the site-specific recombinase recognition sites will be killed.

However, as shown in the examples, the excision of the marker gene by endogenous site-specific recombinases according to the process of the first aspect of the invention is, surprisingly, efficient enough that it is generally unnecessary to include a second gene for positive selection. This is an additional advantage of the invention.

The process of the first aspect of the invention described above may further comprise the step of introducing the nucleic acid molecule into the cell. Methods of transforming prokaryotic cells and transfecting eukaryotic cells are well known in the art and are described, for example in Sambrook (Molecular Cloning; A Laboratory Manual, Second Edition, 1989).

The nucleic acid molecule comprising the selectable marker gene flanked by site-specific recombinase recognition sites, preferably dif-like sites, according to the process of the first aspect of the invention is preferably a linear DNA cassette integrated into the chromosome of the cell or a plasmid.

Where the nucleic acid molecule comprising the selectable marker gene is a linear DNA cassette integrated into the chromosome of the cell, the process of the first aspect of the invention removes the selectable marker gene from the chromosome and can therefore be used as part of a process for unlabelled nucleic acid integration into the chromosome of a cell.

According to a second aspect of the invention, there is provided a process for unlabelled nucleic acid integration into the chromosome of a cell comprising:
a) introducing a linear DNA cassette into a cell, wherein said linear DNA cassette comprises:
    i) a selectable marker gene;
    ii) two site-specific recombinase recognition sites flanking said selectable marker gene; and
    iii) two regions flanking said site-specific recombinase recognition sites which are homologous to the two regions flanking the site of integration in the chromosome of the cell;
b) culturing said cell under conditions such that the linear DNA cassette is integrated into the cell chromosome by homologous recombination; and
c) culturing said cell under conditions such that an endogenous site-specific recombinase in the cell acts to excise the selectable marker gene by site-specific recombination between the site-specific recombinase recognition sites.

The cells, site-specific recombinase recognition sites, site-specific recombinases and selectable marker genes employed in the process of the second aspect of the invention are the same as those described in respect of the process of the first aspect of the invention. In particular, the site-specific recombinase recognition sites are preferably dif-like sites.

The process according to the second aspect of the invention may be used for unlabelled gene deletion or unlabelled gene integration and the nature of the nucleic acid molecule will change accordingly. Where the process of the second aspect of the invention is used for deletion of an endogenous gene, the two regions flanking the site-specific recombinase recognition sites, preferably dif-like sites, are homologous to the two regions flanking the gene to be deleted. Where the process according to the second aspect of the invention is used for the integration of an exogenous gene, the two regions flanking the site-specific recombinase recognition sites, preferably dif-like sites, are homologous to the two regions flanking the site of integration and the linear DNA cassette further comprises the exogenous gene to be integrated, provided that the exogenous gene is not located between the two site-specific recombinase recognition sites. It will be apparent to the skilled person that the exogenous gene to be integrated cannot be located between the site-specific recombinase recognition sites as this would result in the exogenous gene being excised by endogenous site-specific recombinases along with the selectable marker gene.

The process according to the second aspect of the invention may be used not just to delete entire genes but also to delete portions of genes and regulatory regions of genes. Similarly, it may be used to integrate portions of exogenous genes rather than complete exogenous genes.

The research potential of being able to integrate nucleic acid molecules and thus delete endogenous genes or integrate exogenous genes by homologous recombination has been extensively documented in the prior art. The advantage of the process of the invention over prior art methods is that it allows nucleic acid integration to take place without leaving a selectable marker gene behind and without the need to introduce an exogenous recombinase in trans to promoter removal of the selectable marker gene, as required by current processes in the art.

The linear DNA cassette used in the process of the second aspect of the invention may be produced by constructing a plasmid comprising the required elements and linearising the plasmid using a restriction endonuclease. Alternatively, the linear DNA cassette may be assembled by PCR, which produces linear DNA, where the PCR primers contain sequence in their 5' ends that is homologous to the chromosomal target. Competent cells of the target strain are then made and transformed or transfected with linearised plasmid DNA or a PCR product.

The conditions required for integration of the DNA cassette by homologous recombination will vary according to the cell used in the process of the invention. In particular, the conditions required for integration of a linear DNA cassette vary in prokaryotic cells. To integrate the linear DNA cassette into the target chromosome of *B. subtilis*, simple transformation and clone selection (e.g. by antibiotic resistance) is sufficient. In *E. coli*, however, the RecBCD enzyme rapidly degrades linear DNA, so chromosomal integration using a RecBCD$^-$ strain can be used (Jasin and Schimmel, 1984; Winas et al., 1985) followed by P1 transduction into a RecBCD$^+$ strain if desired (Williams et al., 1998). Where the target strain is RecA$^-$, a helper plasmid expressing recA may be necessary. An alternative is to use a helper plasmid expressing the lambda Red functions bet, exo and gam; these inhibit RecBCD and allow chromosomal integration even the absence of RecA (Murphy, 1998).

Preferably, step b) of the process of the second aspect of the invention further comprises culturing the cell in the presence of a selective pressure on the selectable marker gene. Culturing the cell in the presence of selective pressure on the selectable marker gene allows selection of cells in which the linear DNA cassette has integrated into the chromosome. Where the selectable marker gene is an antibiotic resistance gene, this step comprises culturing the cells in the presence of an antibiotic. Preferably, step c) comprises culturing the cell in the absence of any selective pressure, e.g. in the absence of antibiotic. Culturing of cells in the absence of selective pressure allows survival of cells from which the selectable marker gene has been excised. FIG. 1 provides a summary of a preferred process of the second aspect of the invention. The nucleic acid molecule may further comprise a gene for positive selection of cells in which recombination has taken place, as described in relation to the process of the first aspect of the invention. However, as indicated previously, excision of the selectable marker gene by endogenous site-specific recombinases is efficient enough that a gene for positive selection of cells in which recombination has taken place is not generally necessary.

According to a third aspect of the invention, the nucleic acid molecule comprising the selectable marker gene referred to in the process of the first aspect of the invention is a plasmid. According to a preferred embodiment of this aspect of the invention, there is provided a process for the removal of a selectable marker gene from a plasmid comprising introducing a plasmid comprising a selectable marker gene flanked by site-specific recombinase recognition sites into a cell and culturing said cell under conditions such that an endogenous site-specific recombinase acts to excise the selectable marker gene from the plasmid by site-specific recombination between the site-specific recombinase recognition sites.

The cells, site-specific recombinase recognition sites, site-specific recombinases and selectable marker genes employed in the process of the third aspect of the invention are the same as those described in respect of the processes of the first aspect of the invention. In particular, the site-specific recombinase recognition sites are preferably dif-like sites.

Where the cell according to the third aspect of the invention is a prokaryotic cell, it is preferably a RecA+ cell. In the industrial manufacture of plasmid DNA for applications such as DNA vaccines or gene therapy, there are stringent regulations on the proportion of the product that is supercoiled, monomeric DNA. These requirements mean that plasmid DNA has always been grown in RecA$^-$ strains, as homologous recombination due to RecA generates plasmid multimers that reduce the proportion of monomeric plasmid. However, RecA$^+$ strains are significantly more viable than RecA strains, as RecA is essential for repairing stalled replication forks that occur during chromosome replication. In a culture of a RecA$^-$ strain, up to 50% of the cells will not contain a chromosome (Cox et al., 2000). The presence of site-specific recombinase recognition sites, in particular dif-like sites, in the plasmids used in the process of the third aspect of the invention allow the plasmid to be produced in RecA+ cells without plasmid multimerisation occurring.

Preferably, the cell is cultured in the presence of selective pressure on the selectable marker gene and is subsequently cultured in the absence of selective pressure on the selectable marker gene. Culturing the cell in the presence of selective pressure allows selection of cells containing the plasmid. The removal of selective pressure on the selectable marker gene allows survival of cells from which the selectable marker gene has been excised. The nucleic acid molecule may further comprise a gene for positive selection of cells in which recombination has taken place, as described in relation to the process of the first aspect of the invention. However, as indicated previously, excision of the selectable marker gene by endogenous site-specific recombinases is efficient enough that a gene for positive selection of cells in which recombination has taken place is not generally necessary.

Preferably, the process of the third aspect of the invention further comprises maintaining the plasmid in the cell by means of an alternative system not dependent on a selectable marker gene. Preferably, the cell and the plasmid are constructed such that, following removal of the selectable marker gene, the plasmid is capable of being maintained by an alternative maintenance system that is not dependent on the selectable marker gene. Preferably, where the selectable marker gene according to the third aspect of the invention is an antibiotic resistance gene, the process according to the third aspect of the invention allows selection of transformed cells containing the plasmid in the presence of the antibiotic and, following deletion of the antibiotic resistance gene, allows maintenance of the plasmid by an antibiotic-free system.

Preferably, the antibiotic-free system that allows maintenance of the plasmid following removal of the antibiotic resistance gene is operator repressor titration (ORT). Where ORT is used to maintain the plasmid following deletion of the antibiotic resistance gene, the plasmid further comprises an operator susceptible to binding by a repressor and the cell further comprises a first gene present on the chromosome encoding said repressor and a second gene present on the chromosome that is essential for cell growth and is functionally associated with the same operator that is present on the plasmid. In the absence of the plasmid, the repressor binds to the operator upstream of the essential second gene, thereby inhibiting expression of the essential gene such that there is no cell growth. In contrast, when the plasmid is present in sufficient numbers, the operator on the plasmid titrates the repressor such that the essential gene is expressed and the cells grow. ORT is described in detail in WO97/09435, Hanak and Cranenburgh, 2001 and Cranenburgh et al., 2001. Any of the essential genes, operator sequences and repressor sequences referred to in WO97/09435, Hanak and Cranenburgh, 2001 and Cranenburgh et al., 2001 may be used in the cells and plasmids of the present invention to allow maintenance of the plasmid following deletion of the antibiotic resistance gene.

Preferably, the plasmid comprises the lac operator and the cell comprises a first gene encoding the lac repressor present on the chromosome and a second gene present on the chromosome that is essential for cell growth and is functionally associated with the lac operator. The process according to this second aspect of the invention is illustrated in FIG. 2 where the lac operator is included on the plasmid.

An additional application for the processes of the invention is in the regulation of gene expression. The regulation of gene expression is important as a low level of expression prior to induction can lead to a metabolic burden or toxic effects from the recombinant protein, thus reducing or inhibiting cell growth and significantly reducing yield. In prokaryotes and eukaryotes, a promoter must be adjacent to a gene or an operon for effective transcription. Traditionally, regulation of gene expression has been achieved by using a second gene that expresses a repressor protein that binds to an operator in the promoter region of the gene of interest, blocking its expression. Expression of the gene of interest is thus controlled by controlling the expression of the repressor. Alternatively, transcription terminators are inserted between the promoter and the transgene of interest expression preventing expression. The transcription terminators or the gene cassette is flanked by site-specific recombination sites such that expression of the gene in the cassette is prevented until the exogenous site specific recombinase gene is expressed, thus bringing the promoter in close proximity to the transgene and enabling gene expression. However, both these strategies encounter problems with low level expression of the exogenous site-specific recombinase or the repressor. These problems are avoided by the use of endogenous site-specific recombinases that act on site-specific recombinase recognition sites, preferably dif-like sites, to control the expression by recombination event when an external selection pressure (e.g. antibiotic selection) is removed.

According to a fourth aspect of the invention, there is therefore provided a process for controlling expression of a gene of interest comprising culturing a cell comprising:
i) a first nucleic acid molecule comprising a gene of interest that is functionally associated with an operator; and
ii) a second nucleic acid molecule comprising a selectable marker gene and a repressor gene flanked by site-specific recombinase recognition sites, wherein said repressor is susceptible of binding to said operator
under conditions such that an endogenous site-specific recombinase in the cell acts to excise the selectable marker gene and said repressor gene by site-specific recombination between the site-specific recombinase recognition sites, thereby permitting expression of a gene of interest.

The first and second nucleic acid molecules used in this process may be plasmid DNA or linear DNA cassettes integrated in the chromosome of the cell. Preferably, both nucleic acid molecules are linear cassettes integrated into the chromosome of the cell. Alternatively, the first nucleic acid molecule may be a linear DNA cassette integrated into the chromosome of the cell and the second nucleic acid molecule may be a plasmid, or vice versa.

According to a second embodiment of the fourth aspect of the invention, there is provided a process for controlling expression of a gene of interest comprising culturing a cell comprising a nucleic acid molecule comprising
i) a gene of interest functionally linked to a promoter; and
ii) a selectable marker gene and a transcription terminator flanked by site-specific recombinase recognition sites, wherein said selectable marker gene and transcription terminator flanked by site-specific recombinase recognition sites are located between the gene of interest and the promoter controlling expression of said gene of interest
under conditions such that an endogenous site-specific recombinase in the cell acts to excise the selectable marker gene and said transcription terminator by site-specific recombination between the site-specific recombinase recognition sites, thereby permitting expression of a gene of interest.

The cells, site-specific recombinase recognition sites, site-specific recombinases and selectable marker genes employed in the process of the fourth aspect of the invention are the same as those described in respect of the process of the first aspect of the invention. In particular, the site-specific recombinase recognition sites are preferably dif-like sites. The nucleic acid molecule may be a plasmid or may be a linear DNA cassette integrated in the chromosome.

Preferably, the cell is cultured in the presence of selective pressure on the selectable marker gene followed by removal of the selective pressure. This embodiment is shown in FIGS. 3 and 4. The nucleic acid molecule may further comprise a gene for positive selection of cells in which recombination has taken place, as described in relation to the process of the first aspect of the invention.

The processes of the first, second, third and fourth aspects of the invention may also be carried out to remove a selectable marker gene from a nucleic acid molecule in vitro. For example, the process may be used in vitro to remove a selectable marker gene from a plasmid prior to introducing it into a cell. In these circumstances, the plasmid may contain a second gene that allows positive selection of cells containing the plasmid following its introduction into a cell. According to a fifth aspect of the invention, there is provided a process for removing a selectable marker gene from a nucleic acid molecule in vitro comprising supplying a nucleic acid molecule comprising a selectable marker gene flanked by site-specific recombinase recognition sites, preferably dif-like sites, with a site-specific recombinase that acts to excise the selectable marker gene by site-specific recombination between the site-specific recombinase recognition sites. The site-specific recombinase supplied in the process of the fifth aspect of the invention may be any of these prokaryotic or eukaryotic recombinases which are known to act at site-specific recombinase recognition sites, preferably dif-like sites, as described previously.

The invention further provides host cells and nucleic acid molecules for use in the processes of the invention described above.

According to a sixth aspect of the invention, there is provided a nucleic acid molecule comprising a selectable marker gene flanked by site-specific recombinase recognition sites. Suitable site-specific recombinase recognition sites and selectable marker genes for inclusion in the nucleic acid molecules of the sixth aspect of the invention are discussed above in connection with the process of the first aspect of the invention. Preferably, the site-specific recombinase recognition sites are dif-like sites. Preferably the nucleic acid molecule is a linear DNA cassette or a plasmid. Where the nucleic acid molecule is a linear DNA cassette, it preferably further comprises regions of homology that are homologous to regions flanking the chromosomal location at which it is intended to be integrated. The linear DNA cassette may further comprise an exogenous gene. Where the nucleic acid molecule is a plasmid, it may further comprise an operator sequence so that the plasmid can be maintained by ORT following deletion of the selectable marker gene.

According to a seventh aspect of the invention, there is provided a cell comprising a nucleic acid molecule according to the sixth aspect of the invention. The cell may be a prokaryotic cell or a eukaryotic cell. Suitable cells include cells discussed in relation to the process of the first aspect of the invention above. Where the cell comprises a plasmid comprising an operator for maintenance by ORT after deletion of the selectable marker gene, the cell may preferably comprise a first gene present on the chromosome encoding the repressor that binds to the operator on the plasmid and a second gene present on the chromosome that is functionally associated with the same operator and essential for cell growth, as described in more detail above. Where the cell comprising a plasmid is a prokaryotic cell, it may be a RecA+ cell. As noted above, the presence of the site-specific recombinase recognition sites, preferably dif-like sites, on the plasmids of the invention enables them to be cultured in RecA+ cells without the problem of multimerisation (FIG. 5).

According to an eighth aspect of the invention, there is therefore provided a process for producing a supercoiled, monomeric plasmid DNA in a RecA+ cell comprising culturing a RecA+ cell comprising a plasmid, characterised in that the plasmid comprises a site-specific recombinase recognition site, preferably a dif-like site. The presence of the site-specific recombinase recognition site, preferably dif-like site, prevents the problem of multimerisation (FIG. 5), thereby allowing supercoiled monomeric DNA which meets regulatory requirements to be produced. Suitable site-specific recombinase recognition sites, preferably dif-like sites, for including in the plasmid in the process of the eighth aspect of the invention are described above. Preferably, the RecA+ cell is an *E. coli* cell.

The invention will now be described in more detail by way of example with reference to chromosomal gene deletion and integration. It will be appreciated that modifications may be made to the systems described in the Examples.

EXAMPLES

Example 1

Unlabelled Chromosomal Gene Deletion

This example illustrates how the msbB gene (Somerville et al., 1995) was deleted from the *E. coli* chromosome to generate a new strain with a reduced endotoxin activity.

Figure 1:
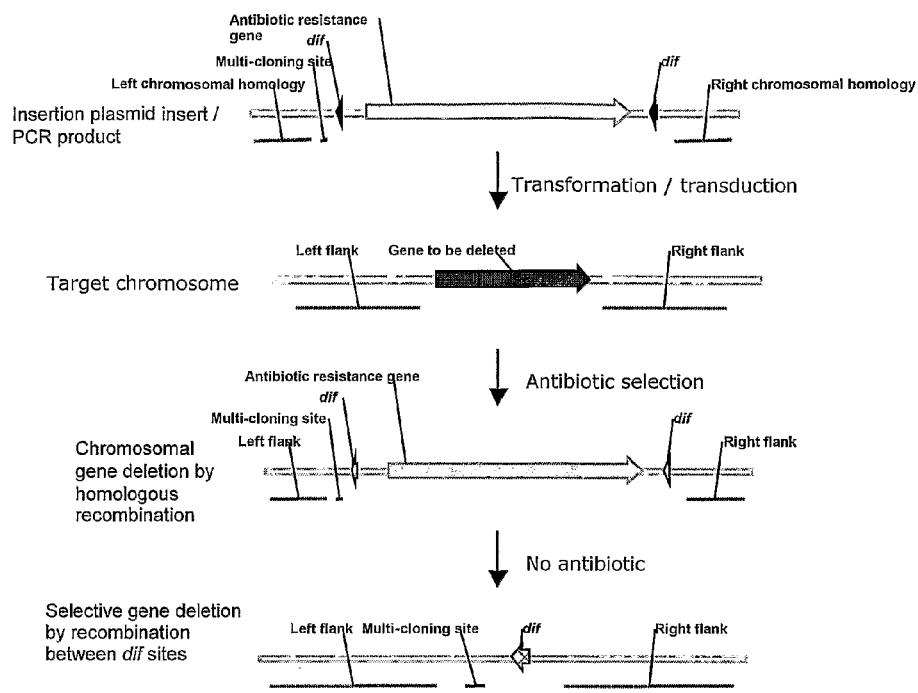
FIG. 1: Gene deletion and selectable marker excision using site-specific recombination at dif sites. For gene insertion, a gene can be cloned into the multi-cloning site and the insertion site can be an intergenic region if required.
Figure 2:
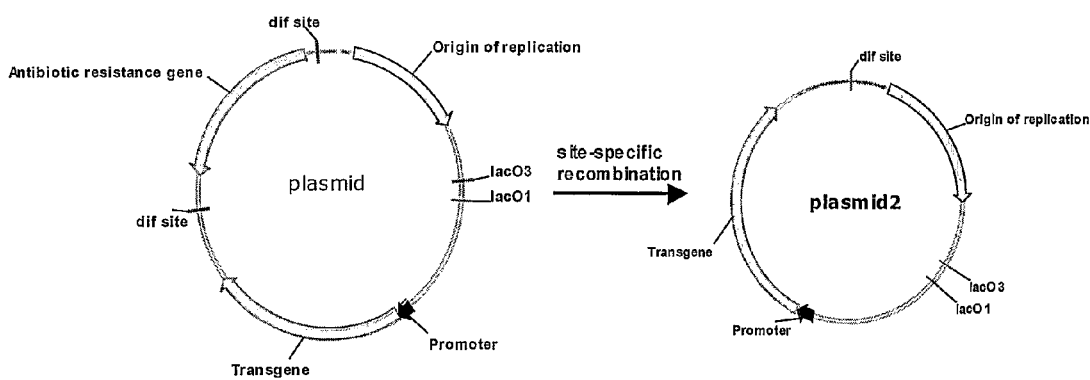
FIG. 2: Selectable marker excision from a plasmid using site-specific recombination at dif sites following the removal of the selection pressure (e.g. antibiotic).
Figure 3:
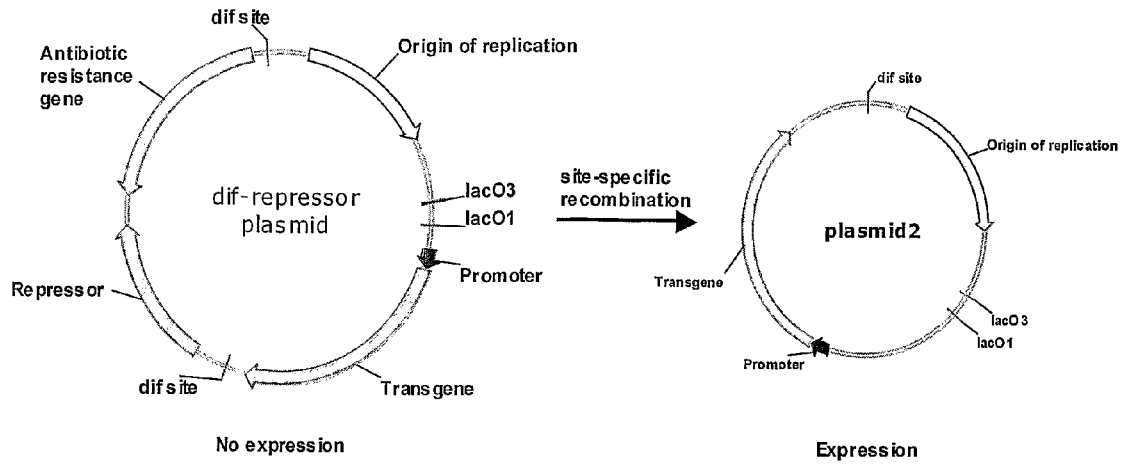
FIG. 3: Selectable marker and repressor excision from a plasmid using site-specific recombination at dif sites following the removal of the selection pressure (e.g. antibiotic). With the repressor gene removed, the expression of the transgene from the promoter becomes constitutive.
Figure 4:
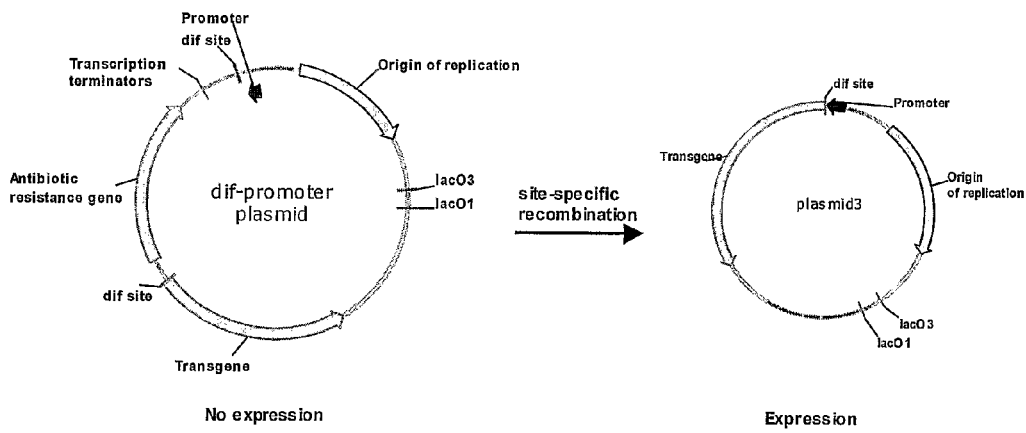
FIG. 4: Selectable marker excision from a plasmid using site-specific recombination at dif sites following the removal of the selection pressure (e.g. antibiotic) to bring a transgene under the control of an upstream promoter. Transgene expression is prevented by a gene cassette consisting of an antibiotic resistance gene and transcription terminators placed between the promoter and the transgene. With this cassette removed by recombination between dif sites, the expression of the transgene from the promoter is enabled.
Figure 5:
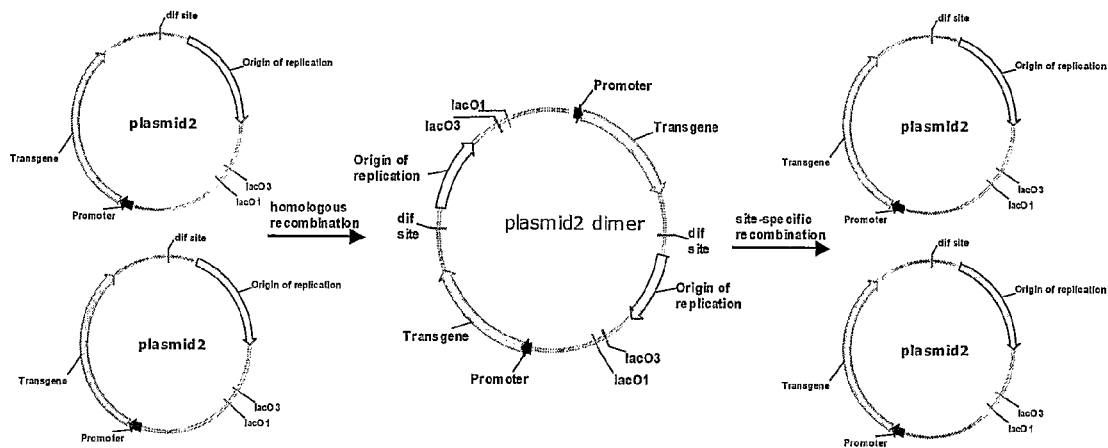
FIG. 5: Resolution of plasmid multimers in RecA+ cells. RecA converts plasmid monomers to dimers by homologous recombination. If a dimer resolution site dif (e.g. cer and its accessory sequences) is present, the native site-specific recombinases (e.g. XerC and XerD) will convert this dimer back to a monomeric form.
Figure 6:
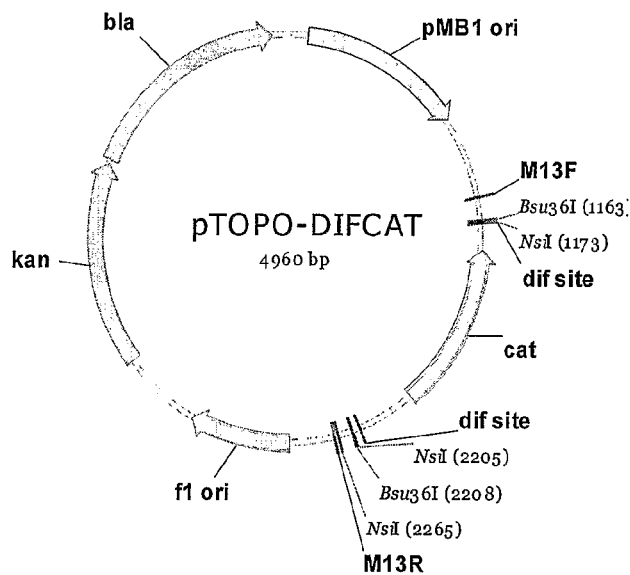
FIG. 6: The primers 5DIFCAT and 3DIFCAT were used to amplify cat and incorporate flanking dif sites. This was cloned into pTOPO to create the precursor deletion plasmid pTOPO-DIFCAT.

Firstly, the chloramphenicol resistance gene cat was amplified from the plasmid pKO3 (Link et al., 1997) using primers 5DIFCAT and 3DIFCAT. These 81 nt primers incorporated a 3' region of homology flanking the cat gene in pKO3 with a 5' tail that included a 28 bp dif site and the restriction sites Bsu36I and NsiI. This PCR product was cloned in to pC2.1 (Invitrogen) using the TOPO cloning method to create a precursor gene deletion plasmid, pTOPO-DifCAT (FIG. 6).

To create a strain with an msbB gene deletion, the dif-cat-dif cassette from pTOPO-DIFCAT was amplified by PCR using primers with 5' ends homologous to the chromosomal regions flanking msbB (msb.int F and msb.int R) to create the DifCAT PCR product. The *E. coli* strain DH1 was transformed with the tetracycline-selectable plasmid pTP223 that provides the lambda Red gene functions for protection and integration of linear DNA (Murphy, 1998). DH1(pTP223) was then transformed with the DifCAT PCR product, and integrants (DH1:DifCATΔmsbB) were selected on chloramphenicol.

Figure 7:
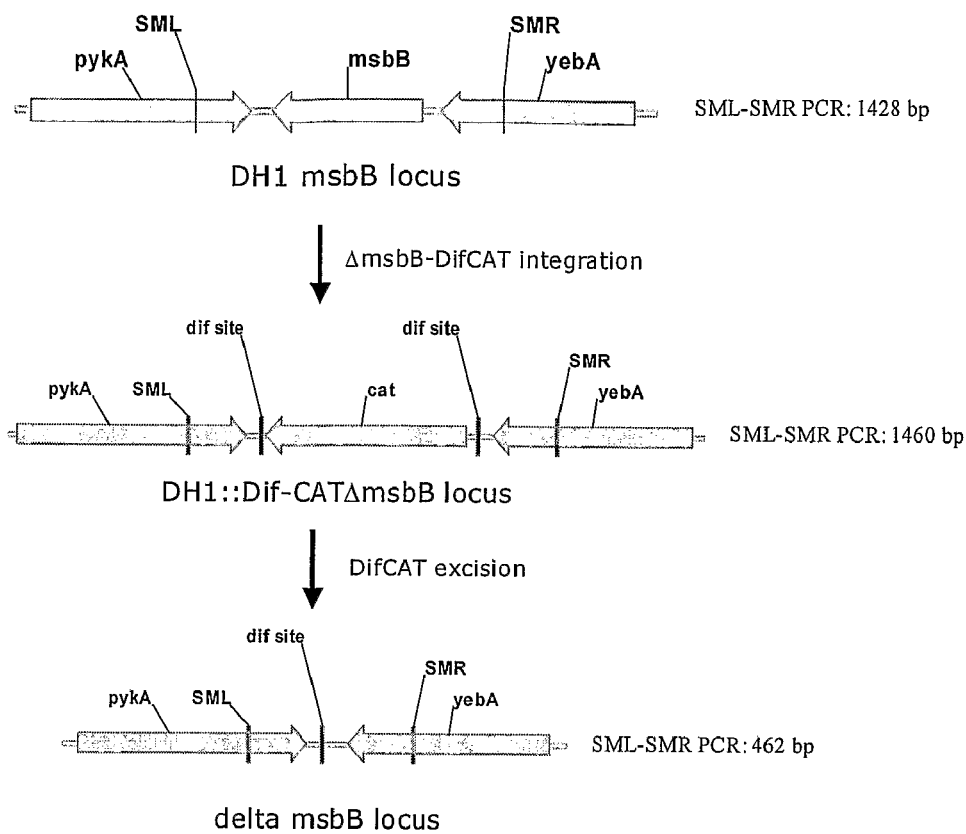
FIG. 7: A) Diagram of the wild-type, integrant and resolvant loci during the chromosomal deletion of msbB. B) Agarose gel of PCR products generated using primers SML and SMR. The wild-type msbB locus gives a product of 1428 bp. Integration of the ΔmsbB-ADifCAT cassette results in an increase in size to 1460 bp, and cat excision at dif sites results in the final, 462 bp PCR product.
Figure 7:
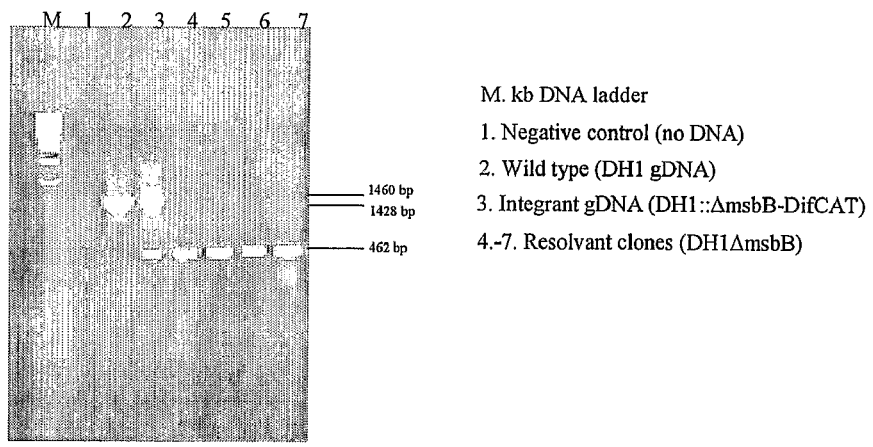

Primers SML and SMR were used to amplify a part of the msbB locus by diagnostic PCR (FIG. 7). In wild-type DH1, this gave a product of 1428 bp for the native msbB locus (lane 2). The integrant locus was 1460 bp, but this PCR also amplified a product of 462 bp, indicating an msbB deletion, as a proportion of the population underwent XerCD-mediated recombination even in the presence of chloramphenicol (lane 3). Subculture in the absence of antibiotics resulted in the loss of pTP223 and the generation of resolvant, chloramphenicol-sensitive clones with only the 462 bp msbB deletion locus detected by PCR (lanes 4-7). The deletion of msbB was confirmed by DNA sequencing.

Example 2

Unlabelled Chromosomal Gene Insertion

This example shows the insertion of an exogenous gene, the bovine pancreatic ribonuclease gene rbpA, into a chromosomal space between two native genes (ubiB and fadA) in *E. coli* strain DH1lacdapD.

The plasmid prbpA-DifCAT was constructed with rbpA adjacent to Dif-CAT from pTOPO-DifCAT. prbpA-DifCAT was used as a PCR template with the 70 nt primers Int F and Int R. The 20 bp at the 3' end of each primer was homologous to the template and there was a 50 bp 5' tail with homology to the target ubiB-fadA locus. A PCR integration fragment of 1691 bp was produced and transformed into DH1lacdapD (pTP223) to create the integrant DH1lacdapD:rbpA-DifCAT (pTP223).

Figure 8:
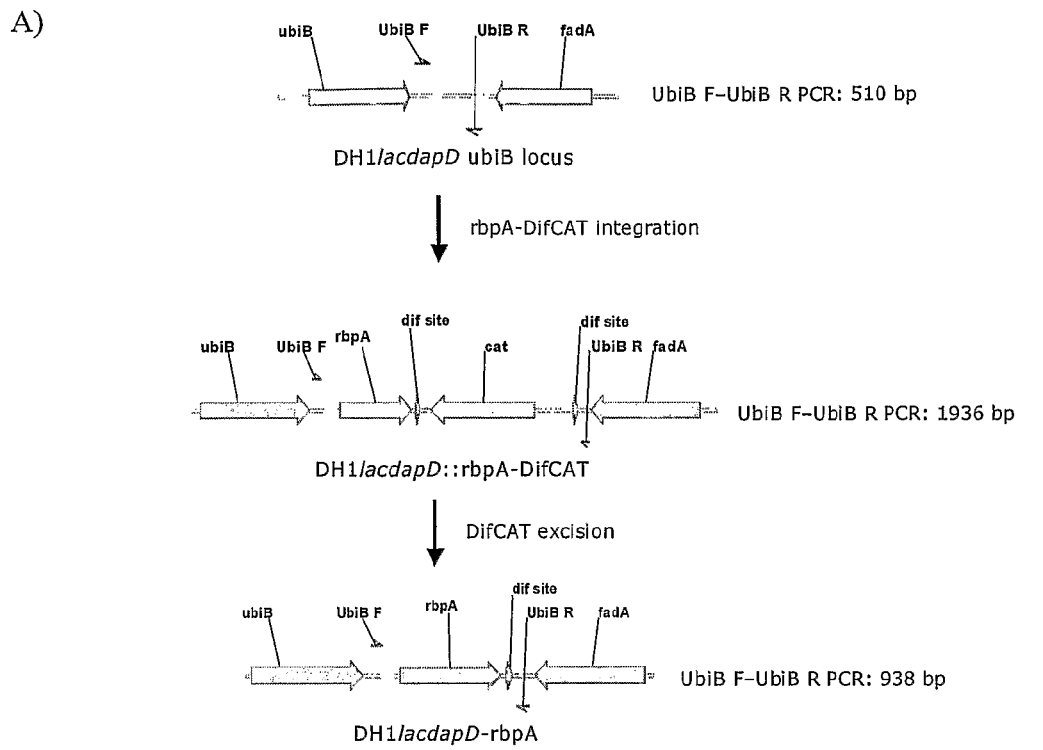
FIG. 8: A) Diagram of the wild-type, integrant and resolvant loci during the chromosomal integration of rbpA. B) Agarose gel of PCR products generated using primers Int F and Int R. The wild-type integration locus between ubiB and fadR gives a product of 510 bp. Integration of the rbp-DifCAT cassette results in an increase in size to 1936 bp, and cat excision at dif sites results in the final, 938 bp PCR product.
Figure 8:
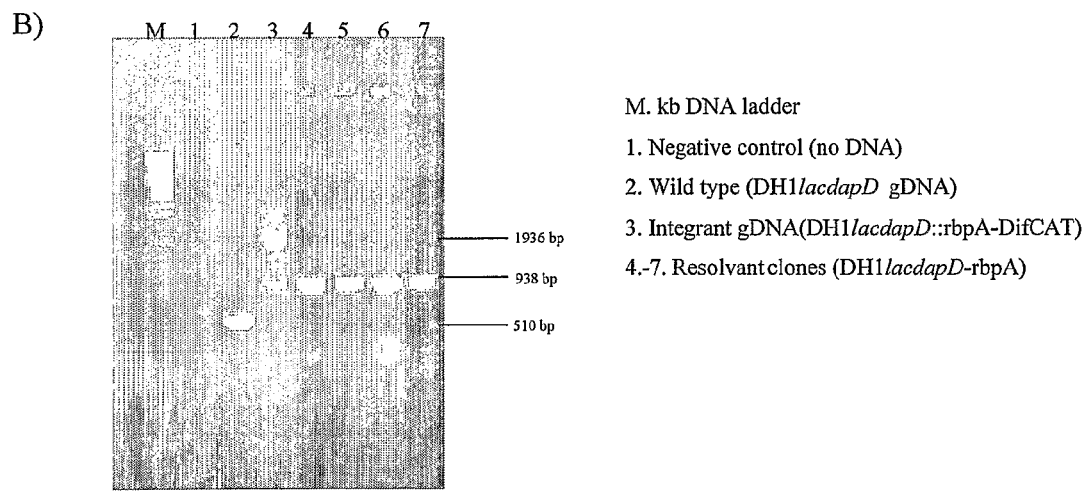

Primers UbiB F and UbiB R were used to amplify a part of the ubiB-fadA locus by diagnostic PCR (FIG. 8). In wild-type DH1lacdapD, this gave a product of 510 bp for the native msbB locus (lane 2). The integrant locus was 1936 bp, but this PCR also amplified a product of 938 bp, indicating an rbpA insertion, as a proportion of the population underwent XerCD-mediated recombination even in the presence of chloramphenicol (lane 3). The integrant strain was cured of the helper plasmid pTP223 and the cat gene excised from DH1lacdapD by culturing without antibiotics, and the integrated rbpA gene detected as a 938 bp PCR product (lanes 4-7). The insertion of rbpA was confirmed by DNA sequencing.

Example 3

Estimation of Gene Excision Frequencies

This example determines the frequency of XerCD-mediated recombination at dif sites, measured by the excision of dif-flanked antibiotic resistance genes integrated into two chromosomal loci of *E. coli* DH1.

Two integrant strains (DH1:ΔmsbB-DifCAT and DH1:rbpA-DifCAT) were used, with dif-flanked chloramphenicol resistance genes inserted in different chromosomal loci (msbB and ubiB-fadA loci respectively). These were inoculated in triplicate into 5 ml LB broth containing 20 μg ml$^{-1}$ chloramphenicol and grown throughout the day until an optical density ($OD_{600}$) of approximately 0.5. Shake flasks containing 50 ml LB broth were inoculated to a starting $OD_{600}$ of 0.005. The shake flasks were incubated at 37° C. with shaking at 200 r.p.m. for a 24-hour period. After the first 24-hour growth period, the $OD_{600}$ was recorded and a calculated volume was used to inoculate another 50 ml shake flask, again to give a starting OD of 0.005. This subculturing procedure was repeated at 24-hour intervals for a total period of 96 hours. The number of generations from each of the six flasks was calculated upon subculture.

After 48 and 96 hours growth, the cultures were serially diluted in LB broth and plated onto LB agar to produce single colonies. To estimate the frequency of XerCD-mediated recombination at the dif sites, 100 colonies for each of the six cultures were replica streaked onto LB agar+/−20 μg ml$^{-1}$ chloramphenicol. Clones that had become chloramphenicol sensitive were screened by PCR using diagnostic PCR primers to amplify the modified region of the locus (SML and SMR primers for the msbB locus; UbiB F and UbiB R for the ubiB-fadA locus). The resulting data were used to calculate the XerCD-mediated antibiotic resistance gene excision frequencies, as shown in Table 2.

TABLE 2

Gene excision frequencies by Xer site-specific recombination at dif sites. Frequencies are reported at two time-points for the excision of a chloramphenicol resistance gene.

| | Gene excision in msbB locus | | Gene excision in ubiB-fadA locus | |
| --- | --- | --- | --- | --- |
| | Time (hours) | | | |
| | 48 | 96 | 48 | 96 |
| Generations | 19.7 | 39.2 | 18.7 | 37.9 |
| Excision frequency | 6.3% | 7.0% | 1.0% | 2.8% |

These data illustrate that after only two days of culturing integrant strains, the excision frequency is sufficiently high (1-6%) that less than 100 colonies need to be screened to identify the desired recombinant.

Appendix: Primers

```
Primers are written 5' to 3'.
5DIFCAT(SEQ ID NO: 6):
CCTTAGGATGCATGGTGCGCATAATGTATATTATGTTAAATCCCTTATGC

GACTCCTGCATCCCTTTCGTCTTCGAATAAA

3DIFCAT(SEQ ID NO: 7):
CCTTAGGATGCATATTTAACATAATATACATTATGCGCACCATCCGCTTA

TTATCACTTATTCAGGCGTAGCACCAGGCGT

Msb-int F(SEQ ID NO: 8):
TGCGGCGAAAACGCCACATCCGGCCTACAGTTCAATCATAGTTCAACAGA

AGTGTGCTGGAATTCGCCCT

Msb-int R(SEQ ID NO: 9):
TTGGTGCGGGGCAAGTTGCGCCGCTACACTATCACCAGATTGATTTTTGC

ATCTGCAGAATTCGCCCTTA

IntF(SEQ ID NO: 10):
AAACCCGCCCCTGACAGGCGGGAAGAACGGCAACTAAACTGTTATTCAGT

TTGCGCCGACATCATAACGG
```

```
Int R(SEQ ID NO: 11):
GCCGGATGCGGCGTGAACGCCTTATCCGGTCTACCGATCCGGCACCAATG
GCTACGGTTTGATTAGGGAA

SML(SEQ ID NO: 12):
TGACCTGGTGATTGTCACCC

SMR(SEQ ID NO: 13):
TAAACCAGCAGGCCGTAAAC

UbiB F(SEQ ID NO: 14):
GATCGCCTGTTTGGCGATGC

UbiB R(SEQ ID NO: 15):
GAATCTGATGGAACGCAAAG
```

REFERENCES

Barre, F.-X., Aroyo, M., Colloms, S. D., Helfrich, A., Cornet, F. and SheiTatt, D. J., 2000. FtsK functions in the processing of a Holliday junction intermediate during bacterial chromosome segregation. *Genes & Dev.* 14: 2976-2988.

Bregu, M., Sherratt, D. J. and Colloms, S. D., 2002. Accessory factors determine the order of strand exchange in Xer recombination at psi. *EMBO J.* 21: 3888-3897.

Cornet, F., Mortier, I., Patte, J. and Louarn, J.-M., 1994. Plasmid pSC101 harbors a recombination site, psi, which is able to resolve plasmid multimers and to substitute for the analogous chromosomal *Escherichia coli* site dif. *J. Bacteriol.* 176, 3188-3195.

Cranenburgh, R. M., Hanak, J. A. J., Williams, S. G., and Sherratt, D. J. (2001). *Escherichia coli* strains that allow antibiotic-free plasmid selection and maintenance by repressor titration. *Nucleic Acids Res.* 29: e26.

Cox, M. M., Goodman, M. F., Kreuzer, K. N., Sherratt, D. J., Sandler, S. J., Marians, K. J., 2000. The importance of repairing stalled replication forks. *Nature* 404: 37-41.

Dale, E. C. and Ow, D. W., 1991. Gene transfer with subsequent removal of the selection gene from the host genome. *Proc. Natl. Acad. Sci. USA* 88: 10558-10562.

Datsenko, K. A. and Wanner, B. L., 2000. One-step inactivation of chromosomal genes in *Escherichia coli* K-12 using PCR products. *Proc. Natl. Acad. Sci. USA* 97: 6640-6645.

Hanak, J. A. J. and Cranenburgh, R. M., 2001. Antibiotic free plasmid selection and maintenance in bacteria. In *Recombinant protein production with prokaryotic and eukaryotic cells.* Kluwer Academic Publishers. p. 111-124.

Jasin, M. and Schimmel, P., 1984. Deletion of an essential gene in *Escherichia coli* by site-specific recombination with linear DNA fragments. *J. Bacteriol.* 159: 783-786.

Leenhouts, K., Buist, G., Bolhuis, A., ten Berge, A., Kiel, J., Mierau, I., Dabrowska, M., Venema, G. and Kok, J., 1996. A general system for generating unlabelled gene replacements in bacterial chromosomes. *Mol. Gen. Genet.* 253: 217-224.

Leslie, N. R. and Sherratt, D. J., 1995. Site-specific recombination in the replication terminus region of *Escherichia coli*: functional replacement of dif. *EMBO J.* 14: 1561-1570.

Link, A. J., Phillips, D. and Church, G. M., 1997. Methods for generating precise deletions and insertions in the genome of wild-type *Escherichia coli*: application to open reading frame characterization. *J. Bacteriol.* 1997: 6228-6237.

McCulloch, R., Coggins, L. W., Colloms, S. D. and Sherratt, D. J., 1994. Xer-mediated site-specific recombination at cer generates Holliday junctions in vivo. *EMBO J.* 13: 1844-1855.

Murphy, K. C., 1998. Use of bacteriophage λ recombination functions to promote gene replacement in *Escherichia coli*. *J. Bactiol.* 180: 2063-2071.

Recchia, G. D., Aroyo, M., Wolf, D., Blakely, G and Sherratt, D. J., 1999. FtsK-dependant and -independent pathways of Xer site-specific recombination. *EMBO J.* 18: 5724-5734.

Sanchis, V., Agaisse, H., Chaufaux, J. and Lereclus, D., 1997. A recombinase-mediated system for elimination of antibiotic resistance gene markers from genetically engineered *Bacillus thuringiensis* strains. *Appl. Environ. Microbiol.* 63: 779-784.

Sciochetti, S. A., Piggot, P. J. and Blakely, G. W., 2001. Identification and characterisation of the dif site from *Bacillus subtilis*. *J. Bacteriol.* 183: 1058-1068.

Somerville, J. E., Cassiano, L., Bainbridge, B., Cunningham, M. D. and Darveau, R. P., 1995. A novel *Escherichia coli* lipid A mutant that produces an antiinflammatory lipopolysaccharide. *J. Clin. Invest.* 97: 359-365.

Sugita, K., Kasahara, T, Matsunaga, E, Ebinuma, H, 2000. A transformation vector for the production of marker-free transgenic plants containing a single copy transgene at high frequency. *Plant J.* 22:461-469.

Williams, S. G., Cranenburgh, R. M., Weiss, A. M. E., Wrighton, C. J., Sherratt, D. J. and Hanak, J. A. J., 1998. Repressor titration: a novel system for selection and maintenance of recombinant plasmids. *Nucleic Acids Res.*, 26: 2120-2124.

Winans S. C., Elledge S. J., Krueger, J. H., Walker, G. C., 1985. Site-Directed Insertion and Deletion Mutagenesis with Cloned Fragments in *Escherichia coli*. *J. Bacteriol.*, 161: 1219-1221.

The invention claimed is:

1. A process for unlabelled nucleic acid integration into the chromosome of a prokaryotic cell comprising:
   introducing a linear DNA cassette into a prokaryotic cell, wherein said linear DNA cassette comprises:
   a selectable marker gene;
   two dif-like site-specific recombinase recognition sites flanking said selectable marker gene; and
   two regions flanking said dif-like site-specific recombinase recognition sites which are homologous to the two regions flanking the site of integration in the chromosome of the cell;
   culturing said cell under conditions such that the linear DNA cassette is integrated into the cell chromosome by homologous recombination to produce a cell comprising said DNA cassette; and
   culturing said cell comprising said DNA cassette under conditions such that an endogenous site-specific recombinase encoded by the chromosome of the cell acts to excise the selectable marker gene by site-specific recombination between the dif-like site-specific recombinase recognition sites.

2. A process according to claim 1 wherein the cell is a bacterial cell.

3. A process according to claim 2 wherein the cell is a gram negative bacterial cell.

4. A process according to claim 2 wherein the cell is a gram positive bacterial cell.

5. A process according to claim 3 wherein the cell is an *E. coli* cell.

6. A process according to claim 4 wherein the cell is a *B. subtilis* cell.

7. A process according to claim 2 wherein the cell is a RecA+cell.

8. A process according to claim 1 wherein the dif-like site-specific recombinase recognition sites flanking the selectable marker gene are the same.

9. A process according to claim 1 wherein the dif-like site-specific recombinase recognition sites flanking the selectable marker gene are different.

10. A process according to claim 1 wherein at least one of the dif-like sites is selected from the *E.coli* dif site and the *B. subtilis* dif site.

11. A process according to claim 1 wherein at least one of the dif-like sites is selected from the plasmid dif-like sites cer and psi and the DNA cassette further comprises accessory sequences that are required for the site-specific recombinase to act.

12. A process according to claim 1 wherein at least one of the dif-like sites is the hybrid dif-like site pif and the DNA cassette further comprises accessory sequences that are required for the site-specific recombinase to act.

13. A process according to claim 1 wherein the selectable marker gene is an antibiotic resistance gene.

14. A process according to claim 1 for unlabelled gene deletion wherein the two regions flanking said dif-like site-specific recombinase recognition sites are homologous to the two regions flanking the gene to be deleted in the chromosome of the cell.

15. A process according to claim 1 for unlabelled gene integration wherein the two regions flanking the dif-like site-specific recombinase recognition sites are homologous to the two regions flanking the site of integration and the linear DNA cassette further comprises the exogenous gene to be integrated, provided that the exogenous gene is not located between the two dif-like site-specific recombinase recognition sites.

16. A process according to claim 1 wherein the step of culturing said cell under conditions such that the linear DNA cassette is integrated into the cell chromosome by homologous recombination further comprises culturing the cell in the presence of a selective pressure on the selectable marker gene.

17. The process according to claim 16 wherein the step of culturing said cell comprising said DNA cassette under conditions such that an endogenous site-specific recombinase present in the chromosome of the cell acts to excise the selectable marker gene by site-specific recombination between the dif-like site-specific recombinase recognition site comprises culturing the cell in the absence of any selective pressure.

18. A process according to claim 1 wherein the DNA cassette further comprises a gene for positive selection of cells in which recombination has taken place.

* * * * *

SEQUENCE LISTING

```
<160> NUMBER OF SEQ ID NOS: 15

<210> SEQ ID NO 1
<211> LENGTH: 28
<212> TYPE: DNA
<213> ORGANISM: Escherichia coli

<400> SEQUENCE: 1
ggtgcgcata atgtatatta tgttaaat                                     28

<210> SEQ ID NO 2
<211> LENGTH: 30
<212> TYPE: DNA
<213> ORGANISM: Escherichia coli
```

-continued

```
<400> SEQUENCE: 2
ggtgcgtaca attaagggat tatggtaaat                                           30

<210> SEQ ID NO 3
<211> LENGTH: 27
<212> TYPE: DNA
<213> ORGANISM: Salmonella

<400> SEQUENCE: 3
gtgcgcgcaa gatccattat gttaaac                                              27

<210> SEQ ID NO 4
<211> LENGTH: 28
<212> TYPE: DNA
<213> ORGANISM: Artificial Sequence
<220> FEATURE:
<223> OTHER INFORMATION: pif site (dif-psi hybrid)

<400> SEQUENCE: 4
ggtgcgcgca agatccatta tgttaaat                                             28

<210> SEQ ID NO 5
<211> LENGTH: 28
<212> TYPE: DNA
<213> ORGANISM: Bacillus subtilis

<400> SEQUENCE: 5
acttcctaga atatatatta tgtaaact                                             28

<210> SEQ ID NO 6
<211> LENGTH: 81
<212> TYPE: DNA
<213> ORGANISM: Artificial Sequence
<220> FEATURE:
<223> OTHER INFORMATION: 5DIFCAT primer

<400> SEQUENCE: 6
ccttaggatg catggtgcgc ataatgtata ttatgttaaa tcccttatgc gactcctgca          60
tccctttcgt cttcgaataa a                                                    81

<210> SEQ ID NO 7
<211> LENGTH: 81
<212> TYPE: DNA
<213> ORGANISM: Artificial Sequence
<220> FEATURE:
<223> OTHER INFORMATION: 3DIFCAT primer

<400> SEQUENCE: 7
ccttaggatg catatttaac ataatataca ttatgcgcac catccgctta ttatcactta          60
ttcaggcgta gcaccaggcg t                                                    81

<210> SEQ ID NO 8
<211> LENGTH: 70
<212> TYPE: DNA
<213> ORGANISM: Artificial Sequence
<220> FEATURE:
<223> OTHER INFORMATION: Msb-int F primer

<400> SEQUENCE: 8
tgcggcgaaa acgccacatc cggcctacag ttcaatgata gttcaacaga agtgtgctgg          60
aattcgccct                                                                 70
```

```
<210> SEQ ID NO 9
<211> LENGTH: 70
<212> TYPE: DNA
<213> ORGANISM: Artificial Sequence
<220> FEATURE:
<223> OTHER INFORMATION: Msb-int R primer

<400> SEQUENCE: 9
ttggtgcggg gcaagttgcg ccgctacact atcaccagat tgattttttgc atctgcagaa    60 ttcgcccttta                                                           70

<210> SEQ ID NO 10
<211> LENGTH: 70
<212> TYPE: DNA
<213> ORGANISM: Artificial Sequence
<220> FEATURE:
<223> OTHER INFORMATION: Int F primer

<400> SEQUENCE: 10
aaacccgccc ctgacaggcg ggaagaacgg caactaaact gttattcagt ttgcgccgac    60
atcataacgg                                                            70

<210> SEQ ID NO 11
<211> LENGTH: 70
<212> TYPE: DNA
<213> ORGANISM: Artificial Sequence
<220> FEATURE:
<223> OTHER INFORMATION: Int R primer

<400> SEQUENCE: 11
gccggatgcg gcgtgaacgc cttatccggt ctaccgatcc ggcaccaatg gctacggttt    60
gattagggaa                                                            70

<210> SEQ ID NO 12
<211> LENGTH: 20
<212> TYPE: DNA
<213> ORGANISM: Artificial Sequence
<220> FEATURE:
<223> OTHER INFORMATION: SML primer

<400> SEQUENCE: 12
tgacctggtg attgtcaccc                                                 20

<210> SEQ ID NO 13
<211> LENGTH: 20
<212> TYPE: DNA
<213> ORGANISM: Artificial Sequence
<220> FEATURE:
<223> OTHER INFORMATION: SMR primer

<400> SEQUENCE: 13
taaaccagca ggccgtaaac                                                 20

<210> SEQ ID NO 14
<211> LENGTH: 20
<212> TYPE: DNA
<213> ORGANISM: Artificial Sequence
<220> FEATURE:
<223> OTHER INFORMATION: UbiB F primer

<400> SEQUENCE: 14
gatcgcctgt ttggcgatgc                                                 20

<210> SEQ ID NO 15
<211> LENGTH: 20
```

```
-continued
<212> TYPE: DNA
<213> ORGANISM: Artificial Sequence
<220> FEATURE:
<223> OTHER INFORMATION: UbiB R primer

<400> SEQUENCE: 15
gaatctgatg gaacgcaaag                                            20
```